United States Patent
Kavarana et al.

(10) Patent No.: US 10,538,790 B2
(45) Date of Patent: Jan. 21, 2020

(54) BIOENZYMATIC SYNTHESIS OF THC-V, CBV AND CBN AND THEIR USE AS THERAPEUTIC AGENTS

(71) Applicant: Teewinot Technologies Limited, Dublin (IE)

(72) Inventors: Malcolm J. Kavarana, Tampa, FL (US); Richard C. Peet, Tampa, FL (US)

(73) Assignee: Teewinot Technologies Limited, Dublin (IE)

( * ) Notice: Subject to any disclaimer, the term of this patent is extended or adjusted under 35 U.S.C. 154(b) by 208 days.

(21) Appl. No.: 15/478,807

(22) Filed: Apr. 4, 2017

(65) Prior Publication Data

US 2017/0283837 A1    Oct. 5, 2017

Related U.S. Application Data

(60) Provisional application No. 62/357,766, filed on Jul. 1, 2016, provisional application No. 62/317,979, filed on Apr. 4, 2016.

(51) Int. Cl.
*C12P 7/22*    (2006.01)
*C07D 311/80*    (2006.01)

(52) U.S. Cl.
CPC .............. *C12P 7/22* (2013.01); *C07D 311/80* (2013.01); *C12Y 121/03007* (2015.07)

(58) Field of Classification Search
None
See application file for complete search history.

(56) References Cited

U.S. PATENT DOCUMENTS

| | | |
|---|---|---|
| 2012/0295968 A1 | 11/2012 | Kelly |
| 2016/0053220 A1 | 2/2016 | Peet et al. |
| 2018/0179564 A1 | 6/2018 | Winnicki et al. |

FOREIGN PATENT DOCUMENTS

| | | |
|---|---|---|
| WO | WO-2014134281 A1 | 9/2014 |
| WO | WO-2017175064 A1 | 10/2017 |

OTHER PUBLICATIONS

ElSohly M et al. Chemical constituents of marijuana: The complex mixture of natural cannabinoids. 2005. Life Sciences. p. 539-548.*
"International Application Serial No. PCT IB2017 000453, International Preliminary Report on Patentability dated Oct. 18, 2018", 10 pgs.
"International Application Serial No. PCT/IB2017/000453, Article 19 Amendments filed Sep. 22, 2017", 5 pgs.
"International Application Serial No. PCT/IB2017/000453, International Search Report dated Jul. 24, 2017", 6 pgs.
"International Application Serial No. PCT/IB2017/000453, Written Opinion dated Jul. 24, 2017", 10 pgs.
F, Taura, et al., "Cannabidiolic-acid synthase, the chemotype-determining enzyme in the fiber-type Cannabis sativa", FEBS Letters, Elsevier, Amsterdam, NL, vol. 581, No. 16, (2007), 2929-2934.
Focella, A, et al., "A simple and practical synthesis of olivetol", J. Org. Chem., vol. 42, No. 21, (1977), 3456-3457.
Futoshi, Taura, et al., "Production of [Delta]I-tetrahydrocannabinolic acid by the biosynthetic enzyme secreted from transgenic Pichi a pastoris", Biochemical and Biophysical Research Communications, Amsterdam, NL ISSN: 0006-291X, XP055389856, (Jun. 23, 2007), 675-680.
Garcia, C, et al., "Symptom-relieving and neuroprotective effects of the phytocannabinoid Δ9-THCV in animal models of Parkinson's disease", Br. J. Pharmacol.,163(7), (2011), 1495-1506.
Taura, Futoshi, et al., "Purification and Characterization of Cannabidiolic-acid Synthase from *Cannabis sativa* L.", The Journal of Biological Chemistry, vol. 271, No. 29,, (1996), 17411-17416.
Vasant, Sandeep, et al., "Promising cannabinoid-based therapies for Parkinson's disease: motor symptoms to neuroprotection", Molecular Neurodegeneration, 10:17, (2015), 26 pgs.
Wargent, E T, et al., "The cannabinoid Δ9-tetrahydrocannabivarin (THCV) ameliorates insulin sensitivity in two mouse models of obesity", Nutr. Diabetes, vol. 3(5), (2013), 1-10.
Booth, Judith K., et al., "Terpene synthases from Cannabis sativa", PLOS One, 12(3), (Mar. 29, 2017), 20 pgs.
Booth, Judith K., et al., "Terpenes in Cannabis sativa—From plant genome to humans", Plant Science 284, (2019), 67-72.

* cited by examiner

*Primary Examiner* — Paul J Holland
(74) *Attorney, Agent, or Firm* — Schwegman, Lundberg & Woessner, P.A.

(57) ABSTRACT

The present invention provides methods for producing cannabinoids. More specifically, the invention is directed to the bio-enzymatic synthesis of THC-v, CBV and CBN by contacting a compound according to Formula I with a cannabinoid synthase enzyme. Also described is a system for producing these pharmaceutically important cannabinoids and the use of such cannabinoids as therapeutic agents.

16 Claims, No Drawings

BIOENZYMATIC SYNTHESIS OF THC-V, CBV AND CBN AND THEIR USE AS THERAPEUTIC AGENTS

CLAIM OF PRIORITY

This application claims the priority benefit of U.S. Patent Application Ser. No. 62/317,979, filed Apr. 4, 2016, and this application also claims the priority benefit of U.S. Patent Application Ser. No. 62/357,766, filed Jul. 1, 2016, each of which is incorporated herein by reference in its entirety.

FIELD OF THE INVENTION

The present invention relates to the biosynthesis of cannabinoids. Specifically, the present invention relates to the synthesis and large-scale production of tetrahydrocannabivarin (THC-v), cannabinol (CBN), and cannabivarin (CBV) and the use of these cannabinoids as therapeutics.

BACKGROUND OF THE INVENTION

Cannabinoids are terpenophenolic compounds found in *Cannabis sativa*, an annual plant belonging to the Cannabaceae family. The plant contains more than 400 chemicals and approximately 70 cannabinoids, which accumulate mainly in the glandular trichomes. The main psychoactive cannabinoid is tetrahydrocannabinol (THC) or more precisely its main isomer (−)-trans-$\Delta^9$-tetrahydrocannabinol ((6aR,10aR)-$\Delta^9$-tetrahydrocannabinol), which is used for treating a wide range of medical conditions, including glaucoma, AIDS wasting, neuropathic pain, treatment of spasticity associated with multiple sclerosis, fibromyalgia and chemotherapy-induced nausea. THC is also effective for treating allergies, inflammation, infection, epilepsy, depression, migraine, bipolar disorders, anxiety disorder, drug dependency and drug withdrawal syndromes.

In addition to THC, other biologically active cannabinoids are also present in *C. sativa* plant. One such cannabinoid is cannabidiol (CBD), an isomer of THC, which is a potent antioxidant and anti-inflammatory compound known to provide protection against acute and chronic neurodegeneration. Another biologically active cannabinoid is cannabigerol (CBG). CBG is found in high concentrations in hemp. It is a high affinity $\alpha_2$-adrenergic receptor agonist, a moderate affinity 5-$HT_{1A}$ receptor antagonist and is a low affinity CB1 receptor antagonist. CBG is known to possess a mild anti-depressant activity. Cannabichromene (CBC) is another biologically active cannabinoid and is known to possess anti-inflammatory, anti-fungal and anti-viral properties. Although many phytocannabinoids are biologically active against the above mentioned disease conditions, the acceptance of phytocannabinoids as candidate therapeutic agents for treating such disease conditions has been slow due to their addictive nature.

Accordingly, efforts have been made to identify phytocannabinoids that retain one or more of the therapeutic properties described above but lack the addictive properties. In this regard, it is known that tetrahydrocannabinolic acid (THCA) and cannabivarin (cannabivarol or CBV) are non-psychoactive, while phytocannabinoids such as tetrahydrocannabivarin (THC-v or THV) and cannabionol (CBN) show mild psychoactive properties.

The naturally low amounts of THC-v, CBV and CBN in the hemp plant *Cannabis sativa* is one important reason why research characterizing the therapeutic and psychoactive properties of these cannabinoids is slow. Additionally, not much is known about the biosynthesis of these cannabinoids or why they are produced at such low levels in the hemp plant.

The present invention addresses many of these questions and provides a method for the bioenzymatic manufacture of THC-v, CBN and CBV and further provides methodologies for the large-scale production of these cannabinoids for therapeutic use.

SUMMARY OF THE INVENTION

The present invention provides a method for producing cannabinoids according to Formula II by (i) contacting a compound according to Formula I, Formula I

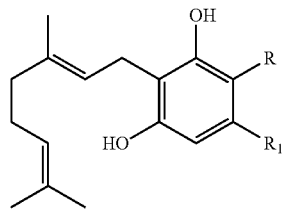

with a cannabinoid synthase in the presence of a solvent to produce a compound according to Formula II:

Formula II

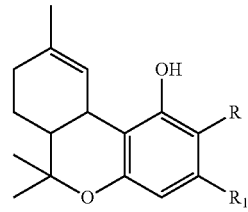

For Formula I and Formula II compounds R is —H, COOH, or —$(CH_2)_n$COOH, substituent $R^1$ is selected from the group consisting of methyl, ethyl, propyl, butyl, pentyl, hexyl, and heptyl; and subscript "n" is 1, 2, 3, 4, 5, or 6.

In one embodiment, cannabinoid synthases used by the inventive method are tetrahydrocannabinolic acid (THCA) synthase, cannabichromene acid synthase (CBCA), or tetrahydrocannabivarin acid (THCVA) synthase.

In one embodiment, for compounds in accordance with the invention substituent R is —COOH and $R^1$ is propyl and the compound according to Formula II is tetrahydrocannabivarin carboxylic acid (THCVA).

In one embodiment of THCVA produced by the inventive method is de-carboxylated to provide tetrahydrocannabivarin (THC-v).

The present invention also provides a method for producing a Formula III compound by contacting a Formula I compound Formula I

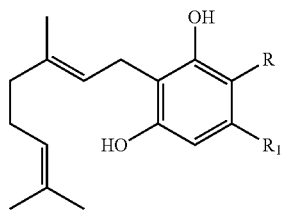

with a cannabinoid synthase in the presence of a solvent to produce a compound according to Formula II; and Formula II

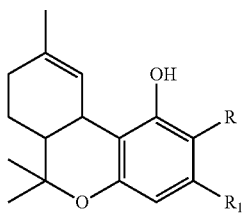

oxidizing the Formula II compound to produce a compound according to Formula III:

Formula III

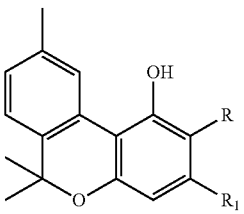

For Formula I, Formula II and Formula III compounds, R is —H, COOH, or —(CH$_2$)$_n$COOH, substituent R$^1$ is selected from the group consisting of methyl, ethyl, propyl, butyl, pentyl, hexyl, and heptyl; and subscript n is 1, 2, 3, 4, 5, or 6.

According to one aspect, the Formula II compounds are de-carboxylated by contacting a solution of the Formula II compound with heat or exposing a solution of the Formula II compound to UV-light.

According to another embodiment, de-carboxylation is carried out by contacting a solution of the Formula III compound with heat or exposing a solution of the Formula III compound to UV-light.

The invention also provides methods for synthesizing a compound according to Formula III by oxidation of a Formula II compound. In one embodiment, when R is —H and R$^1$ is pentyl, the compound according to Formula III is Cannabinol (CBN).

In another embodiment, R is —H and R$^1$ is propyl, the compound according to Formula III is Cannabivarin (CBV).

According to yet another embodiment, the invention provides a system for cannabinoids according to Formula V. According to this embodiment, the inventive system comprises (i) a bioreactor containing a reactant according to Formula IV, a solvent, and a cannabinoid synthase;

Formula IV

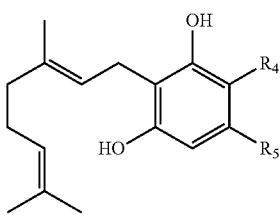

(ii) a control mechanism configured to control at least one condition of the bioreactor, wherein the compound according to Formula IV interacts with the cannabinoid synthase to produce a compound according to Formula V:

Formula V

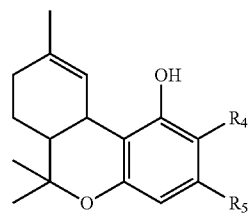

For Formula IV and V compounds substituent R$^4$ is —H, —COOH, —(CH$_2$)$_n$COOH, substituent R$^1$ is selected from the group consisting of methyl, ethyl, propyl, butyl, pentyl, hexyl, and heptyl; and subscript n is 1, 2, 3, 4, 5, or 6.

According to one embodiment, the control mechanism of the bioreactor is configured to control at least one condition that is selected from temperature, solvent, pressure, and pH. For example, in one embodiment, the control mechanism of the bioreactor is configured to control the pH of the reaction mixture in the range from about 4.0 to about 8.0.

As described above, synthesis of cannabinoids using the inventive system comprises the step of contacting a cannabinoid synthase enzyme with a Formula IV compound. In one embodiment, the cannabinoid synthase is tetrahydrocannabivarin acid synthase (THCVA synthase) and the compound according to Formula IV is cannabigerovarin acid (CBGVA) structurally illustrated below:

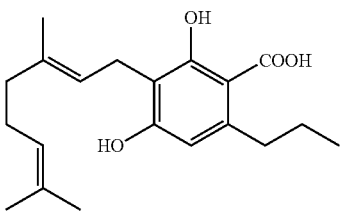 [SMILES: CCCc1cc(O)c(C/C=C(\C)CCC=C(C)C)c(O)c1C(=O)O]

According to this embodiment, the interaction of THCVA synthase with cannabigerovarin acid (CBGVA), a Formula IV compound, produces tetrahydrocannabivarin acid (THCVA, a Formula V compound) structurally illustrated below:

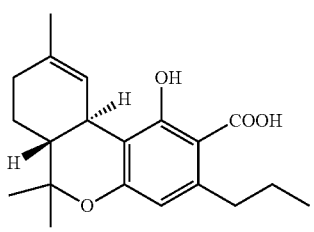 [SMILES: CCCc1cc2c(c(O)c1C(=O)O)[C@@H]1C=C(C)CC[C@H]1C(C)(C)O2]

In one embodiment, THCVA produced using the inventive system may be de-carboxylated to provide tetrahydrocannabivarin (THC-v).

According to yet another embodiment, the invention provides a system for producing cannabinoids according to Formula VI. The inventive system comprises (i) a bioreactor containing a reactant according to Formula IV, a solvent, and a cannabinoid synthase:

Formula IV

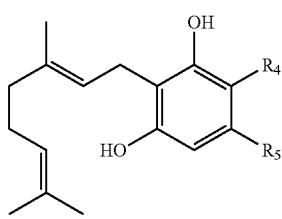

(ii) a control mechanism configured to control at least one condition of the bioreactor, wherein the compound according to Formula IV interacts with the cannabinoid synthase to produce a compound according to Formula V; and Formula V

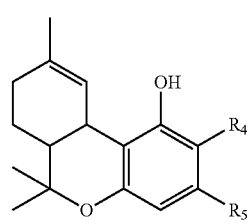

(iii) oxidizing the Formula V compound to produce a compound according to Formula VI:

Formula VI

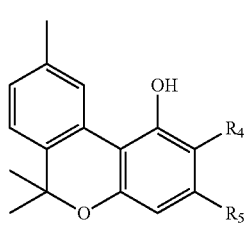

In one embodiment, for compounds in accordance with Formula IV, Formula V and Formula VI, substituent $R^4$ is —H, COOH, or —(CH$_2$)$_n$COOH, substituent $R^5$ is selected from the group consisting of methyl, ethyl, propyl, butyl, pentyl, hexyl, and heptyl; and subscript n is 1, 2, 3, 4, 5, or 6.

In one embodiment, the Formula IV compound is cannabigerolic acid (CBGA) structurally illustrated below:

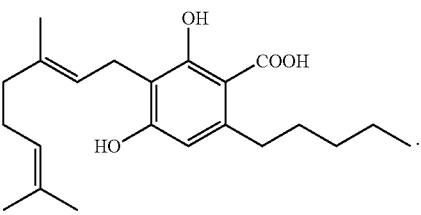 [SMILES: CCCCCc1cc(O)c(C/C=C(\C)CCC=C(C)C)c(O)c1C(=O)O]

According to this embodiment, the system permits the contact of cannabigerolic acid with tetrahydrocannabinolic acid synthase (THCA synthase) to produce the Formula V tetrahydrocabbabinolic acid (THCA) structurally illustrated below:

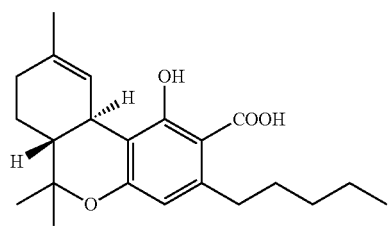 [SMILES: CCCCCc1cc2c(c(O)c1C(=O)O)[C@@H]1C=C(C)CC[C@H]1C(C)(C)O2]

According to a further aspect of this embodiment, THCA produced using the inventive system is oxidized to form cannabinolic acid (CBNA, a Formula VI compound), whose structure is shown below:

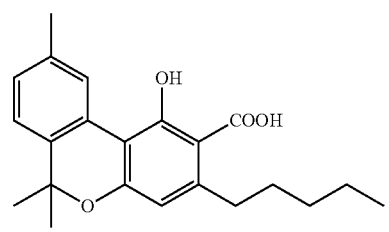 [SMILES: CCCCCc1cc2c(c(O)c1C(=O)O)-c1cc(C)ccc1C(C)(C)O2]

In one embodiment, CBNA is de-carboxylated to produce CBN, whose structure is shown below:

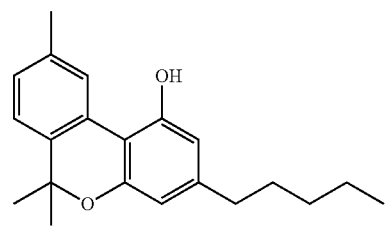 [SMILES: CCCCCc1cc(O)c2c(c1)OC(C)(C)c1ccc(C)cc1-2]

In yet another embodiment the cannabinoid synthase is tetrahydrocannabinolic acid synthase (THCA synthase) and the compound according to Formula IV is cannabigerovarin acid (CBGVA) structurally illustrated below:

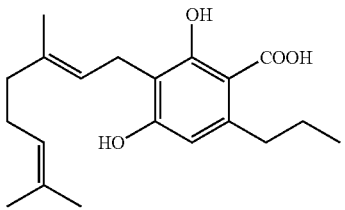 [SMILES: CCCc1cc(O)c(C/C=C(\C)CCC=C(C)C)c(O)c1C(=O)O]

According to this embodiment, the interaction of THCA synthase with cannabigerovarin acid (CBGVA), produces tetrahydrocannabivarin acid (THCVA, a Formula IV compound) structurally illustrated below:

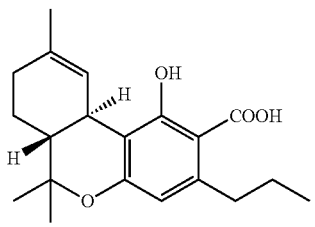 [SMILES: CCCc1cc2c(c(O)c1C(=O)O)[C@@H]1C=C(C)CC[C@H]1C(C)(C)O2]

The THCVA produced using the inventive system may be de-carboxylated to provide tetrahydrocannabivarin (THC-v).

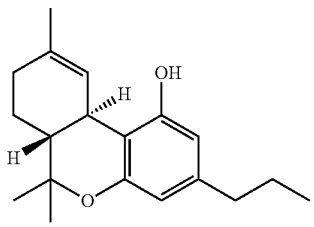 [SMILES: CCCc1cc(O)c2c(c1)OC(C)(C)[C@@H]1CCC(C)=C[C@@H]21]

According to this embodiment, the THC-v is further oxidized to obtain cannabivarin (CBC).

Alternatively, in one embodiment the THCVA is oxidized to obtain cannabivarinic acid, and the cannabivarinic acid is decarboxylated to provide cannabivarin (CBC).

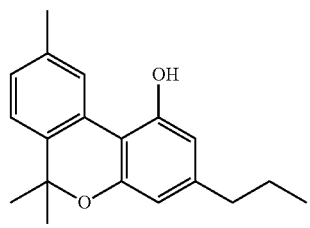 [SMILES: CCCc1cc(O)c2c(c1)OC(C)(C)c1ccc(C)cc1-2]

DETAILED DESCRIPTION

Definitions

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "alkyl" refers to a straight or branched chain, saturated hydrocarbon having the indicated number of carbon atoms. For example, $(C_1\text{-}C_{10})$alkyl is meant to include but is not limited to methyl, ethyl, propyl, isopropyl, butyl, sec-butyl, tert-butyl, pentyl, isopentyl, neopentyl, hexyl, isohexyl, and neohexyl, etc. An alkyl group can be unsubstituted or optionally substituted with one or more substituents as described herein below.

The term "alkenyl" or "alkene" refers to a straight or branched chain unsaturated hydrocarbon having the indicated number of carbon atoms and at least one double bond. Examples of a $(C_2\text{-}C_{10})$alkenyl group include, but are not limited to, ethene, propene, 1-butene, 2-butene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term "alkynyl" refers to a straight or branched chain unsaturated hydrocarbon having the indicated number of carbon atoms and at least one triple bond. Examples of a $(C_2\text{-}C_{10})$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkoxy" refers to an —O-alkyl group having the indicated number of carbon atoms. For example, a $(C_1\text{-}C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aryl" refers to a 3- to 14-member monocyclic, bicyclic, tricyclic, or polycyclic aromatic hydrocarbon ring system. Examples of an aryl group include naphthyl, pyrenyl, and anthracyl. An aryl group can be unsubstituted or optionally substituted with one or more substituents as described herein below.

The terms "alkylene," "cycloalkylene," "alkenylene," "alkynylene," "arylene," and "heteroarylene," alone or as part of another substituent, means a divalent radical derived from an alkyl, cycloalkyl, alkenyl, alkynyl, aryl, or heteroaryl group, respectively, as exemplified by —$CH_2CH_2CH_2CH_2$—. For alkylene, alkenylene, or aryl linking groups, no orientation of the linking group is implied.

The term "halogen" and "halo" refers to —F, —Cl, —Br or —I.

The term "heteroatom" is meant to include oxygen (O), nitrogen (N), and sulfur (S).

A "hydroxyl" or "hydroxy" refers to an —OH group.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —CH$_2$CH$_2$CH$_2$CH$_2$CH$_2$OH,
—CH$_2$CH$_2$CH$_2$CH$_2$CH$_2$CH$_2$OH, and branched versions thereof.

The term "cycloalkyl" or "carbocycle" refer to monocyclic, bicyclic, tricyclic, or polycyclic, 3- to 14-membered ring systems, which are either saturated, unsaturated or aromatic. The heterocycle may be attached via any heteroatom or carbon atom. Cycloalkyl include aryls and hetroaryls as defined above. Representative examples of cycloalky include, but are not limited to, cycloethyl, cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term "nitrile or cyano" can be used interchangeably and refer to a —CN group which is bound to a carbon atom of a heteroaryl ring, aryl ring and a heterocycloalkyl ring.

The term "amine or amino" refers to an —NR$_c$R$_d$ group wherein R$_c$ and R$_d$ each independently refer to a hydrogen, (C$_1$-C$_8$)alkyl, aryl, heteroaryl, heterocycloalkyl, (C$_1$-C$_8$)haloalkyl, and (C$_1$-C$_6$)hydroxyalkyl group.

The term "alkylaryl" refers to C$_1$-C$_8$ alkyl group in which at least one hydrogen atom of the C$_1$-C$_8$ alkyl chain is replaced by an aryl atom, which may be optionally substituted with one or more substituents as described herein below. Examples of alkylaryl groups include, but are not limited to, methylphenyl, ethylnaphthyl, propylphenyl, and butylphenyl groups.

"Arylalkylene" refers to a divalent alkylene wherein one or more hydrogen atoms in the C$_1$-C$_{10}$ alkylene group is replaced by a (C$_3$-C$_{14}$)aryl group. Examples of (C$_3$-C$_{14}$) aryl-(C$_1$-C$_{10}$)alkylene groups include without limitation 1-phenylbutylene, phenyl-2-butylene, 1-phenyl-2-methylpropylene, phenylmethylene, phenylpropylene, and naphthylethylene.

"Arylalkenylene" refers to a divalent alkenylene wherein one or more hydrogen atoms in the C$_2$-C$_{10}$ alkenylene group is replaced by a (C$_3$-C$_{14}$)aryl group.

The term "arylalkynylene" refers to a divalent alkynylene wherein one or more hydrogen atoms in the C$_2$-C$_{10}$ alkynylene group is replaced by a (C$_3$-C$_{14}$)aryl group.

The terms "carboxyl" and "carboxylate" include such moieties as may be represented by the general formula:

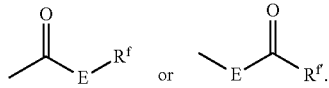

E in the formula is a bond or O and R individually is H, alkyl, alkenyl, aryl, or a pharmaceutically acceptable salt. Where E is O, and R$^f$ is as defined above, the moiety is referred to herein as a carboxyl group, and particularly when R$^f$ is a hydrogen, the formula represents a "carboxylic acid". In general, where the expressly shown oxygen is replaced by sulfur, the formula represents a "thiocarbonyl" group.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% a by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given that structure, then the depicted structure controls. Additionally, if the stereochemistry of a structure or a portion of a structure is not indicated with, for example, bold or dashed lines, the structure or portion of the structure is to be interpreted as encompassing all stereoisomers of it.

In the context of the present invention the term "analog" refers to a compound that is structurally related to naturally occurring cannabinoids, but whose chemical and biological properties may differ from naturally occurring cannabinoids. In the present context, analog or analogs refer compounds that may not exhibit one or more unwanted side effects of a naturally occurring cannabinoid. Analog also refers to a compound that is derived from a naturally occurring cannabinoid by chemical, biological or a semi-synthetic transformation of the naturally occurring cannabinoid.

The term "prodrug" refers to a precursor of a biologically active pharmaceutical agent (drug). Prodrugs must undergo a chemical or a metabolic conversion to become a biologically active pharmaceutical agent. A prodrug can be converted ex vivo to the biologically active pharmaceutical agent by chemical transformative processes. In vivo, a prodrug is converted to the biologically active pharmaceutical agent by the action of a metabolic process, an enzymatic process or a degradative that removes the prodrug moiety to form the biologically active pharmaceutical agent.

The terms "tetrahydrocannabivarin", "THC-v", or "THV" are used interchangeably and refer to the hydrogenated analog of CBV represented as:

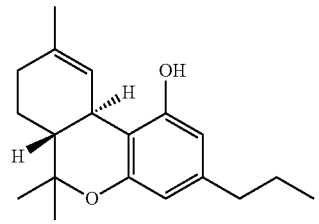 [SMILES: CCCc1cc(O)c2c(c1)OC(C)(C)[C@@H]1CCC(C)=C[C@@H]21]

The terms "cannabivarin", "cannabivarol" and "CBV" are used interchangeably and refer to the oxidized form of THC-v. CBV is a non-psychoactive cannabinoid:

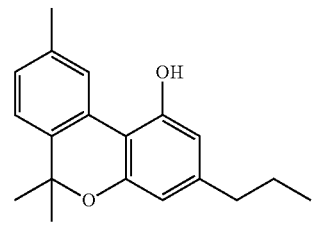 [SMILES: CCCc1cc(O)c2c(c1)OC(C)(C)c1ccc(C)cc1-2]

The terms "cannabinolic acid", or "CBNA" are used interchangeably and refer to the oxidized form of THCA.

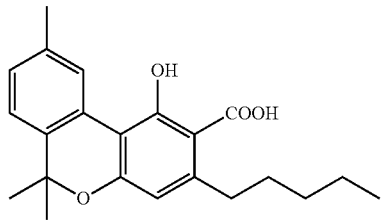 [SMILES: CCCCCc1cc2c(c(O)c1C(=O)O)-c1cc(C)ccc1C(C)(C)O2]

The terms "cannabinol", or "CBN" are used interchangeably and refer to the oxidized form of THC. Cannabinol is a non-psychoactive cannabinoid:

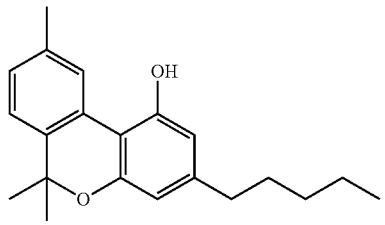 [SMILES: CCCCCc1cc(O)c2c(c1)OC(C)(C)c1ccc(C)cc1-2]

Accordingly, in one of its embodiments the present invention provides the means to synthesize these cannabinoids by contacting a compound according to Formula I Formula I

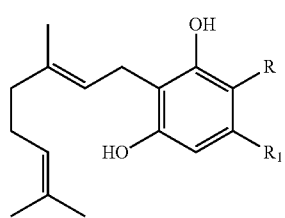

with a cannabinoid synthase in the presence of a solvent to produce a compound according to Formula II, followed by isolation of the Formula II compound:

Formula II

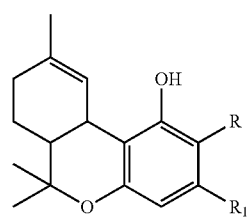

In one embodiment, the inventive method permits oxidizing the Formula II compound to produce a compound according to Formula III:

Formula III

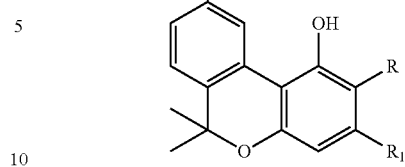

For Formula I, Formula II and Formula III compounds substituent R is —H, —COOH, or —$(CH_2)_n$COOH, substituent $R^1$ is selected from the group consisting of methylene, ethylene, propylene, butylene, pentylene, hexylene, and heptylene, while subscript "n" is 1, 2, 3, 4, 5, or 6.

In one embodiment, $R^1$ is selected from the group consisting of ethyl, propyl, butyl, or pentyl. For instance, $R^1$ is propyl, or pentyl.

According to another embodiment, R is —COOH and $R^1$ is propyl or pentyl. For certain compounds according to the invention, R is —COOH and $R^1$ is propyl. For other Formula I, Formula II and Formula III compounds R is —COOH and $R^1$ is pentyl.

According to another embodiment, R is —H and $R^1$ is propyl or pentyl for compounds of Formula II or Formula III. In one embodiment, R is —H and $R^1$ is propyl for Formula II or Formula III compounds. For certain other Formula II and Formula III compounds, R is —H and $R^1$ is pentyl.

In one embodiment of the invention, for Formula I, Formula II, and Formula III compounds R is —$(CH_2)_n$COOH, $R^1$ is selected from the group consisting of methyl, ethyl, propyl, butyl, and pentyl, and the subscript "n" is 1, 2, 3, or 4. In one embodiment, R is —$(CH_2)_n$COOH, $R^1$ is ethyl, propyl, or pentyl, and the subscript "n" is 1, 2, 3, or 4.

For some Formula I, Formula II and Formula III compounds R is —$(CH_2)_n$COOH, $R^1$ is propyl and "n" is 1 or 2. For other Formula I Formula II and Formula III compounds R is —$(CH_2)_n$COOH, $R^1$ is pentyl and "n" is 1 or 2. In one preferred embodiment, R is —$(CH_2)_n$COOH and $R^1$ is propyl or pentyl.

A Formula II compound according to the inventive method can be modified prior to purification and use. In one embodiment the Formula II compound is decarboxylated (removal of $CO_2$), while according to another aspect of the invention, the modification of a Formula II compound entails oxidizing (dehydrogenation of) the 1-methylcyclohex-1-ene ring of the Formula II compound to obtain a compound according to Formula III.

Decarboxylation of the Formula II compound can occur prior to the oxidation of the 1-methylcyclohex-1-ene ring of the Formula II compound. Accordingly, in one embodiment, the Formula II compound is decarboxylated and then oxidized to a Formula III compound. Alternatively, a Formula II compound is oxidized to a Formula III compound and the resultant Formula III compound is decarboxylated prior to its use as a therapeutic.

The method used to modify the Formula II compound will depend on the nature of the modification desired. In one embodiment the Formula II compound is decarboxylated by contact with heat. According to another embodiment, decarboxylation takes place by contacting a solution of a Formula II compound to heat or exposing a solution of the Formula II compound to UV-light. Alternatively, decarboxylation takes place by contacting a solution of a Formula II or a Formula III compound with a weak base such as sodium bicarbonate.

Solutions of the Formula II compound can be made using organic solvents, aqueous solvents or mixtures of aqueous and organic solvents. Exemplary organic solvents include alcohols, such as methanol, ethanol, propanol, isopropanol, acetone, dimethylsulfoxide, hexane, ethylacetate, PEG, β-cyclodextrin, or any organic solvent in which the Formula II compound is sufficiently soluble.

Illustrative aqueous solvents include without limitation water and aqueous buffers. Buffers typically used in the method of the invention are citrate buffer, phosphate buffer, HEPES, Tris buffer, MOPS, or glycine buffer.

In one embodiment the solvent is a mixture of water and a non-aqueous solvent, or a mixture of an aqueous buffer and a non-aqueous solvent. For such solvent mixtures, the concentration of the non-aqueous solvent may vary between 10% and 90% (v/v). For example, the concentration of the non-aqueous solvent in the reaction mixture is 10%, 20%, 30%, 40%, 50%, 60%, 70%, 80%, or 90%, such as 10%, 12%, 15%, 20%, 25%, 30%, 35%, 40%, 45%, or 50%. In one embodiment the concentration of the non-aqueous solvent in the reaction mixture is about 30%. In another embodiment, the concentration of the non-aqueous solvent in the reaction mixture is about 20%, or may vary between 10% and 20%, between 10% and 30%, or between 10% and 40%.

Methods for oxidizing polycyclic organic compounds are well known in the chemical art. Any such method may be used for oxidizing a Formula II compound to a Formula III compounds, including the use of UV-light, heat, air, oxygen gas, the use of catalysts that promote oxidation, or chemical oxidizing agents provided that the use of such reagents does not alter or destroy the chemical integrity of the inventive Formula II and Formula III compounds.

In one embodiment, the Formula II compound is converted to a Formula III compound by oxidation of the 1-methylcyclohex-1-ene ring of the Formula II compound. Oxidation of the 1-methylcyclohex-1-ene ring of the Formula II compound is accomplished by contacting a stirring solution of the Formula II compound with air.

Alternatively, oxidation is accomplished by prolonged exposure of a solution of the Formula II compound to UV-light or UV-light in the presence of air or oxygen gas. In one embodiment, oxidation of the Formula II compound is accomplished by contacting a solution of the Formula II compound to heat or by contacting a solution of the Formula II compound to heat while simultaneously exposing the stirring solution to air or an atmosphere of oxygen.

In accordance with some embodiments, the invention provides synthetic methodologies for making Formula I compounds from precursor compounds. Thus, one embodiment is illustrated below in Scheme 1, showing the installation of an n-propyl substituent by direct alkylation corresponding to $R^1$ (CDI=1'-carbonyldiimidazole; BTC=bis(trichloromethyl)carbonate).

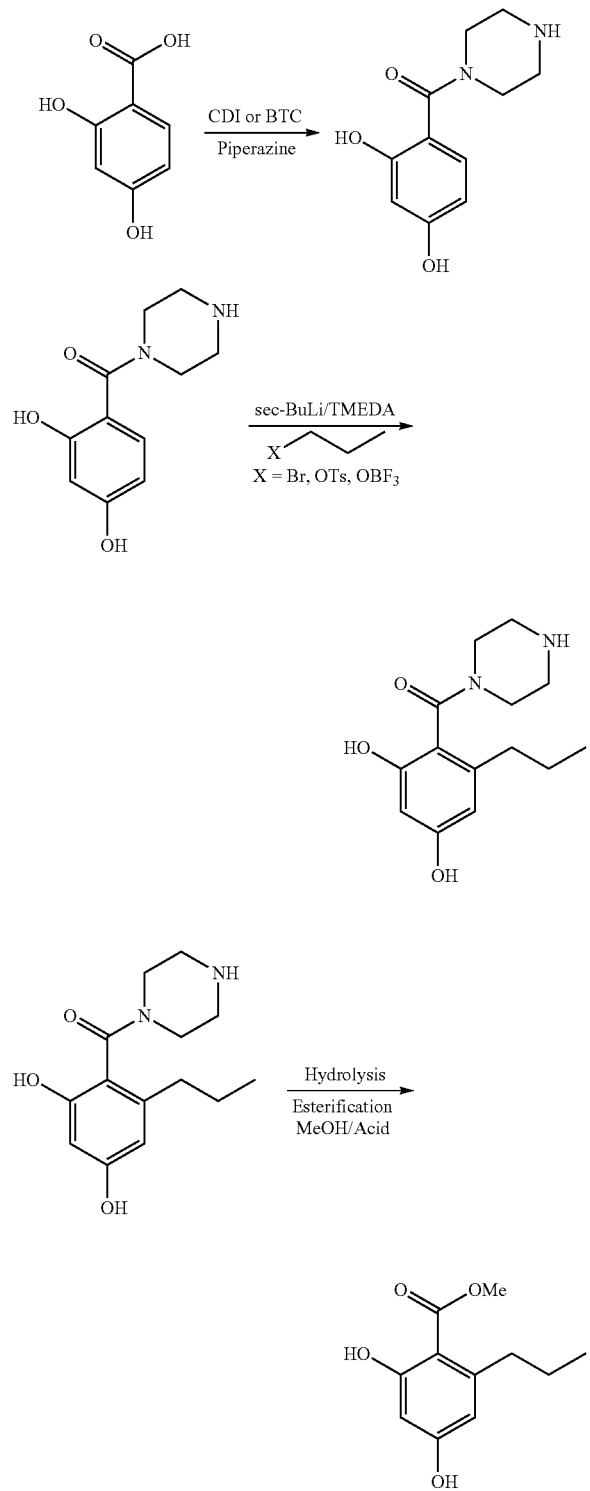

Alternatively, according to another embodiment, the alkyl side chain corresponding to $R^1$ can be installed through a Sonogashira cross-coupling reaction. Illustrating this embodiment is Scheme 2 below, wherein $R^1$ is n-propyl (TBAF=tetrabutylammonium fluoride; and TSAF=tris(dimethylamino)sulfonium difluorotrimethylsilicate).

Scheme 2

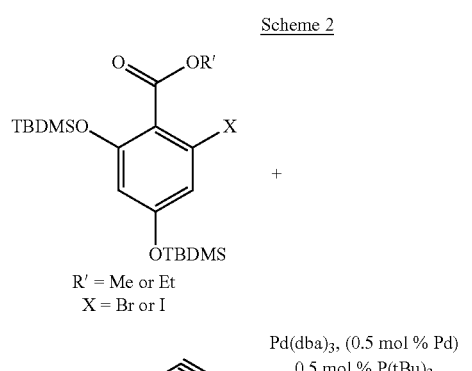

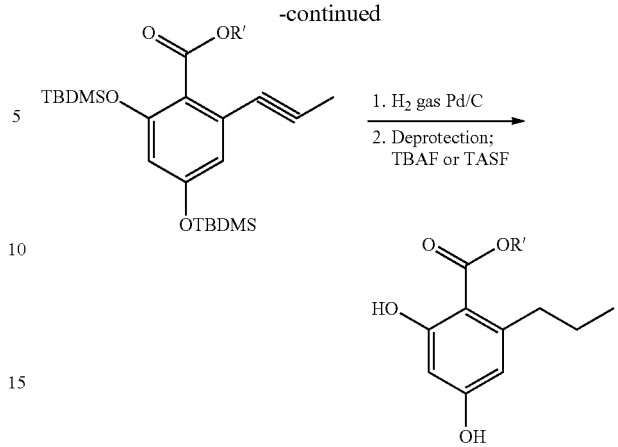

One advantage of the methodology according to this embodiment is the ability to introduce functionality into the $R^1$ side chain. For example, the alkyne group depicted in Scheme 2 can be halogenated by addition of H—X (X=halo) across the triple bond, or the alkyne can be hydroxylated and thereby provide a hydroxyl group that can participate in further reactions. Alternatively, the alkyne can be selectively reduced to an alkene, such as by exposure to a reductant like Na/liquid ammonia.

In accordance with additional embodiments, Formula I compounds are made by synthetic methodologies that are illustrated in Scheme 3 below.

Scheme 3

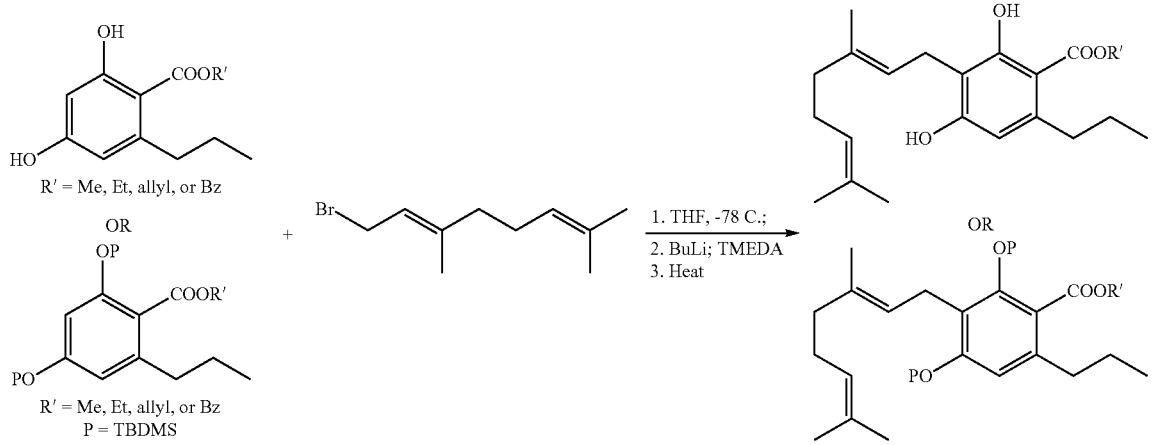

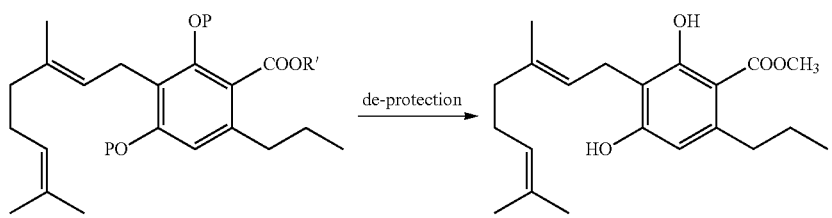

Alternatively, other embodiments of the invention provide different synthetic methodology for making Formula I compounds. These are illustrated in Scheme 3A below.

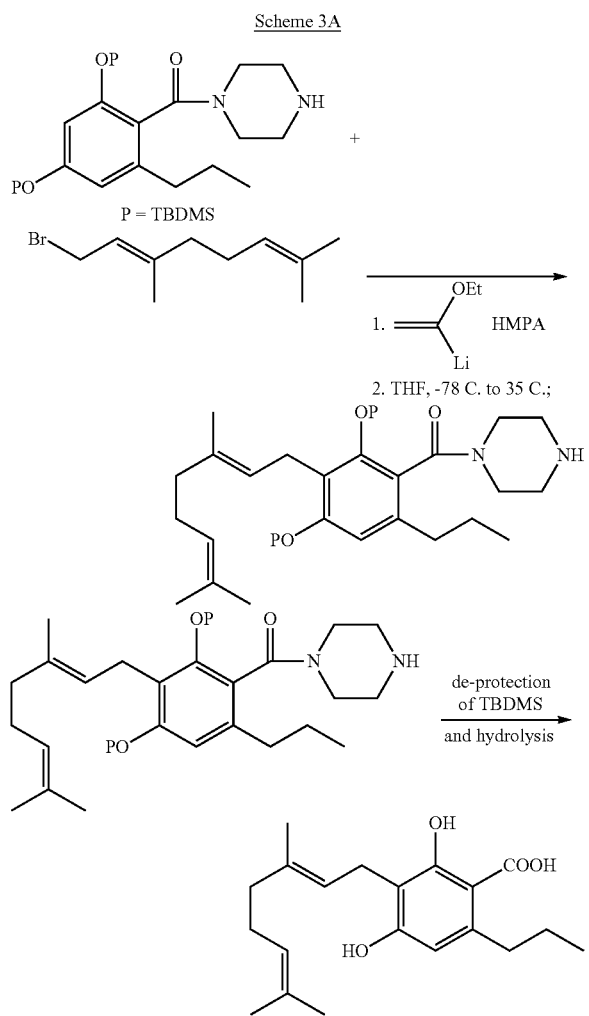

Cannabinoid acid synthase enzymes used to manufacture a cannabinoid according to the inventive method include without limitation tetrahydrocannabinolic acid synthase (THCA synthase), tetrahydrocannabivarin acid (THCVA) synthase, cannabidiolic acid synthase (CBDA synthase), or cannabichromene acid synthase (CBCA synthase). These enzymes are obtained from natural sources or are obtained by recombinant methods using any appropriate microbial expression system including the PichiaPink™ Yeast Expression system described in U.S. Provisional Application No. 62/041,521, filed Aug. 25, 2014 and U.S. patent application Ser. No. 14/835,444, filed Aug. 25, 2015 which published as U.S. Publication No.: 2016-0053220 on Feb. 26, 2016; the contents of both applications are incorporated by reference in their entireties.

In one aspect, the cannabinoid synthase is tetrahydrocannabivarin acid (THCVA) synthase which is contacted with a compound according to Formula I in which R is —COOH or —(CH$_2$)$_n$COOH and R$^1$ is propyl. According to another aspect of the invention, aspect, the cannabinoid synthase is tetrahydrocannabinol acid (THCA) synthase and the compound according to Formula I has substituent R as a —COOH group or —(CH$_2$)$_n$COOH group and R$^1$ as propyl.

Thus, the invention provides a method for synthesizing tetrahydrocannabivarin acid (THCVA) according to Formula II, when R is —COOH. In one embodiment, THCVA is isolated and purified prior to its use as a therapeutic agent. According to this aspect of the invention, THCVA is decarboxylated to THC-v (THV), after it is isolated from the reaction mixture. Alternatively, decarboxylation of THCVA to THC-v is carried out prior to isolating and purifying the crude THC-v.

According to one aspect, THCVA or THC-v synthesized using the inventive method is oxidized to cannabivarin (CBV) using a method described above. CBV is a non-psychoactive cannabinoid found in minor amounts in the hemp plant C. sativa. The present invention therefore provides a novel bioenzymatic method for producing this medicinally important cannabinoid in amounts suitable for pharmaceutical distribution and use. Scheme 4 illustrates the synthesis of THC-v and CBV.

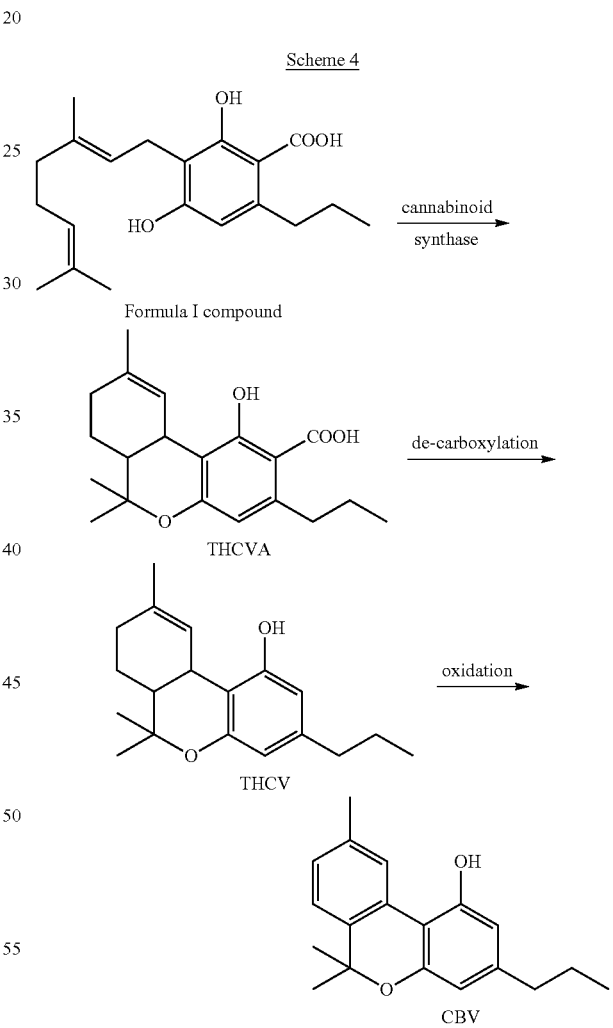

According to yet another aspect, the invention provides a novel method for producing cannabinol (CBN), according to Formula III. CBN which is the oxidized form of THC is obtained by the decarboxylation of cannabinolic acid (CBNA). The synthesis of CBN according to the inventive method, therefore will proceed by contacting a Formula I compound where R is —COOH and R$^1$ is pentyl with the enzyme THCA synthase. The product obtained by this enzyme catalyzed reaction is Δ9-tetrahydrocannabinolic acid (THCA), a Formula II compound, which is oxidized by exposure to air or UV-light to provide cannabinolic acid (CBNA). The therapeutic agent cannabinol (CBN) is produced by decarboxylating CBNA. Scheme 5 illustrates the synthesis of CBN.

between 3.5 and 7.0, between 3.5 and 6.5, between 3.5 and 6.0, between 3.5 and 5.5, between 3.5 and 5.0, or between 3.5 and 4.5.

The cannabinoid according to Formula II or Formula III is purified prior to use. Purification is effected by procedures routinely used in the chemical and biochemical arts, includ-

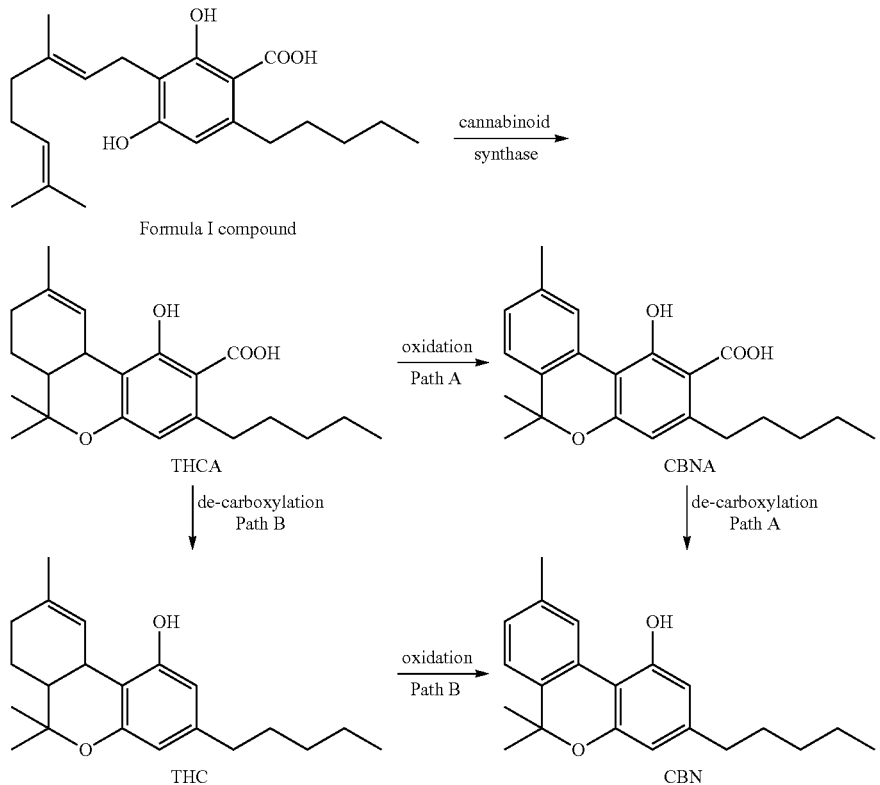

The inventors of the present application unexpectedly discovered that the concentration of the non-aqueous solvent in the reaction mixture can have an effect on the rate of the enzyme-catalyzed reaction as well as the yields of CBV, CBN and THC-v. For example, the presence of cyclodextrins, cyclic oligosaccharides that are amphiphillic in nature, accelerates the rate of the enzyme (cannabinoid synthase) catalyzed cyclization of a Formula I compound.

Another surprising and unexpected observation was that the pH of the reaction mixture can influence the ratio of the cannabinoid products produced using the inventive method. In one embodiment, when a Formula I compound where R is —COOH and $R^1$ is pentyl is contacted with the enzyme THCA synthase the products (Formula II compounds), will be a mixture tetrahydrocannabinolic acid (THCA) or cannabichromene acid (CBCA). The ratio of THCA to CBCA formed depends on the pH of the reaction mixture.

In exemplary embodiments, the bioenzymatic synthesis of CBV, CBN and THC-v according to the inventive method is performed at a pH in a range between 3.0 and 8.0, such as at a pH in a range between 3.0 and 7.0, between 3.0 and 6.0, between 3.0 and 5.0, or between 3.0 and 4.0. In one embodiment, the reaction is performed at a pH in a range between 3.8 and 7.2. According to another embodiment, the pH is in a range between 3.5 and 8.0, between 3.5 and 7.5, ing solvent extraction or chromatographic purification methods. The purity of the purified cannabinoid product is determined by thin layer chromatography, High Performance Liquid Chromatography coupled to a mass spectrometer (HPLC-MS), or by any suitable analytical technique. Nuclear magnetic resonance spectroscopy, mass spectral analysis, or UV, visible spectroscopy, may be used to confirm the identity of the inventive compounds.

Typically, the enantiomeric purity of the inventive compounds is from about 90% ee to about 100% ee. For instance, a cannabinoid according to the present invention can have an enantiomeric purity of about 91% ee, about 92% ee, about 93% ee, about 94% ee, about 95% ee, about 96% ee, about 97% ee, about 98% ee and about 99% ee.

Cannabinoids exert different physiological properties and are known to lessen pain, stimulate appetite and have been tested as candidate therapeutics for treating a variety of disease conditions such as allergies, inflammation, infection, epilepsy, depression, migraine, bipolar disorders, anxiety disorder, and glaucoma. The physiological effects exerted by cannabinoids is due in part to their ability to stimulate or deactivate the cannabinoid receptors, for instance the CB1, CB2 and CB3 receptors.

Large Scale Production of Cannabinoids using a Bioreactor

A bioreactor system is used for the large scale production of a cannabinoid according to one embodiment of the present invention. The bioreactor used for synthesizing a cannabinoid may be configured for batch synthesis or continuous synthesis so as to permit commercial production of the inventive cannabinoids.

In one embodiment, the system produces cannabinoids according to Formula V and Formula VI. The inventive system in one its embodiments comprises (i) a bioreactor containing reaction medium comprising as reactant a compound according to Formula IV, a solvent, and a cannabinoid synthase,

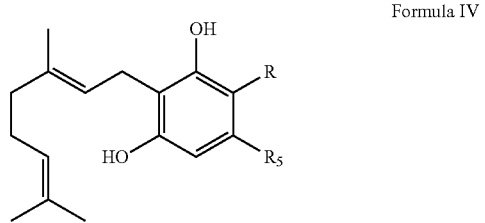

Formula IV (ii) a control mechanism configured to control at least one condition of the bioreactor, wherein the compound according to Formula IV interacts with the cannabinoid synthase to produce a compound according to Formula V,

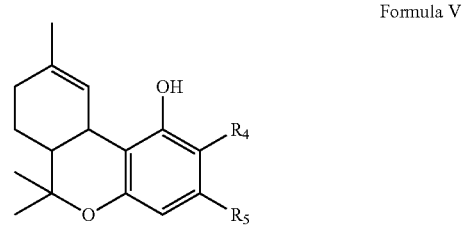

Formula V and the step of
(iii) oxidizing the Formula V compound to produce a compound according to Formula VI.

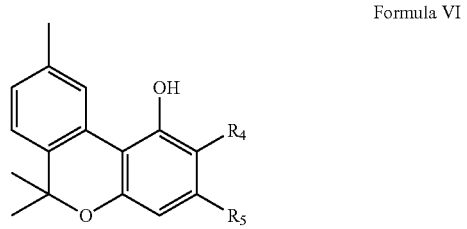

Formula VI

The reactant used for synthesizing cannabinoids using a system of the invention is a Formula IV compound, in which $R^4$ can be —H, COOH, or —$(CH_2)_n$COOH; substituent $R^5$ is selected from the group consisting of methyl, ethyl, propyl, butyl, pentyl, hexyl, and heptyl; and subscript "n" is an integer, such as 1, 2, 3, 4, 5, or 6.

In one embodiment, $R^4$ is —COOH, $R^1$ is propyl and the Formula IV compound is cannabigerovarin acid (CBGVA). According to this embodiment, contacting CBGVA with the enzyme tetrahydrocannabivarin acid synthase (THCVA synthase) will provide the Formula V compound tetrahydrocannabivarin acid (THCVA), which will be decarboxylated to obtain THC-v. The THC-v thus produced may be further oxidized to produce cannabivarin (CBV).

Alternatively, CBGVA will be contacted with the enzyme THCA synthase to produce the compound THCVA which will be decarboxylated to obtain THC-v. The decarboxylation of THCVA can be carried out within the bioreactor, for instance, by exposing the reaction medium of UV-light or increasing the temperature of the bioreactor. Alternatively, decarboxylation of THCVA may occur after isolating THCVA from the bioreactor by methods similar to those described above or by contacting a solution of THCVA with sodium bicarbonate.

The inventive system also permits the large-scale synthesis of CBN by oxidation of THCA, followed by decarboxylation. Synthesis of CBN using the inventive system was accomplished by contacting CBGA, a Formula IV compound where $R^4$ is COOH and substituent $R^5$ is pentyl with the enzyme THCA synthase. The product of the enzyme-catalyzed reaction was tetrahydrocannabinolic acid (THCA), a Formula V compound. In one aspect, the invention provides a method for oxidizing THCA by exposing a solution of THCA to air or UV-light to produce cannabinolic acid (CBNA). Subsequent decarboxylation of CBNA by the application of heat or by contact with a mild base such as sodium bicarbonate provided CBN.

In one embodiment, the system for producing a cannabinoid comprises a bioreactor that is configured for batch synthesis. Thus, the composition of the medium, concentration of the enzyme and substrate are fixed at the beginning of the bioenzymatic process and not allowed to change during catalysis. Synthesis is terminated when the concentration of the desired product in the medium of the bioreactor reaches a predetermined value or the concentration of substrate falls below a predetermined level, such as to a level where there is no detectable catalytic conversion of substrate to product.

In one embodiment, the cannabinoid acid synthase is His-tagged so as to facilitate separation of the enzyme from the product in the reaction medium by sequestering the His-tagged enzyme onto a nickel containing resin support within the bioreactor.

An alternative to the batch process mode is a continuous process mode in which a defined amount of substrate and medium are continuously added to the bioreactor while an equal amount of medium containing the cannabinoid product being simultaneously removed from the bioreactor to maintain a constant rate for formation of product.

The conditions of the bioreactor can be controlled using a control mechanism. The control mechanism may be coupled to the bioreactor or, alternatively, may interact with the bioreactor wirelessly or remotely. The control mechanism is used to control the conditions such the oxygen level, agitation, pH, and flow of materials (e.g. by controlling at least one pump) into and out of the bioreactor. In some embodiments, the control mechanism is configured to control the conditions of the bioreactor based on information obtained from an optical monitoring system.

The control mechanism can include a processing circuit having a processor and memory device configured to complete or facilitate various processes and functions, such as controlling the pH, temperature, and pressure in the bioreactor, or altering the flow rate of medium into or out of the bioreactor. Such control is generally maintained by a communication link with at least one sensor or a plurality of sensors.

Pharmaceutical Compositions

The compounds of Formula II, or Formula III produced in accordance with the inventive methods or compounds according to Formula V or VI produced using the claimed bioreactor system are administered to a patient or subject in need of treatment either alone or in combination with other compounds having similar or different biological activities. For example, the compounds and compositions of the invention are administered in a combination therapy, i.e., either simultaneously in single or separate dosage forms or in separate dosage forms within hours or days of each other. Examples of such combination therapies include administering the compositions and compounds produced by the inventive method or system with other agents used to treat glaucoma, AIDS wasting, neuropathic pain, treatment of spasticity associated with multiple sclerosis, fibromyalgia and chemotherapy-induced nausea.

Thus, the invention provides a pharmaceutical composition comprising tetrahydrocannabivarin (THC-v), cannabinol (CBN), or cannabivarin (CBV), or a pharmaceutically acceptable solvate, or stereoisomer in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

The inventive compositions can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions in accordance with the invention include without limitation tablets, troches, lozenges, aqueous or oily suspensions, dispersible powders or granules, emulsion, hard or soft capsules, syrups or elixirs.

Encompassed within the scope of the invention are pharmaceutical compositions suitable for single unit dosages that comprise at least one of tetrahydrocannabivarin (THC-v), cannabinol (CBN), or cannabivarin (CBV), or a pharmaceutically acceptable solvate, or stereoisomer and a pharmaceutically acceptable carrier.

Inventive compositions suitable for oral use may be prepared according to any method known to the art for the manufacture of pharmaceutical compositions. For instance, liquid formulations of tetrahydrocannabivarin (THC-v), cannabinol (CBN), or cannabivarin (CBV), can contain one or more agents selected from the group consisting of sweetening agents, flavoring agents, coloring agents and preserving agents in order to provide pharmaceutically elegant and palatable preparations of the inventive prodrug.

For tablet compositions, the active ingredient in admixture with non-toxic pharmaceutically acceptable excipients is used for the manufacture of tablets. Exemplary of such excipients include without limitation inert diluents, such as calcium carbonate, sodium carbonate, lactose, calcium phosphate or sodium phosphate; granulating and disintegrating agents, such as corn starch, or alginic acid; binding agents, for example starch, gelatin or acacia, and lubricating agents, such as magnesium stearate, stearic acid or talc. The tablets can be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the active agent is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, polyoxyethylene stearate, heptadecaethyleneoxycetanol, polyoxyethylene sorbitol monooleate, polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending tetrahydrocannabivarin (THC-v), cannabinol (CBN), or cannabivarin (CBV), or a pharmaceutically acceptable solvate, or stereoisomer in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Syrups and elixirs can be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, or an aqueous suspension. This suspension may be formulated according to the known art using those suitable dispersing or wetting agents and suspending agents. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compositions for parenteral administrations are administered in a sterile medium. Depending on the vehicle used, the concentration of the drug in the formulation, the parenteral formulation can either be a suspension or a solution containing dissolved drug. Adjuvants such as local anesthetics, preservatives and buffering agents can also be added to parenteral compositions.

EXAMPLES

Chemical Synthesis

Example 1: Synthesis of Olivetol

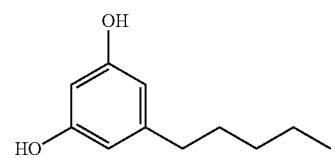

Olivetol was synthesized using a published procedure (Focella, A, et al., *J. Org. Chem.*, Vol. 42, No. 21, (1977), p. 3456-3457).

A. Methyl 6-N-Pentyl-2-hydroxy-4-oxo-cyclohex-2-ene-1-carboxylate

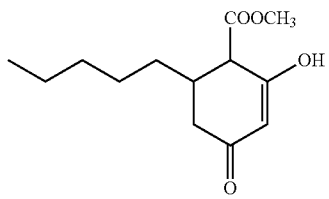 [SMILES: CCCCCC1CC(=O)C=C(O)C1C(=O)OC]

To a stirring solution of sodium methoxide (32.4 g, 0.60 mol) and dimethyl malonate (90 g, 0.68 mol) in 230 mL of anhydrous methanol was added portion wise 75 g (0.48 mol) of 90% 3-nonen-2-one. The reaction mixture was then refluxed for 3 h under $N_2$ and allowed to cool to room temperature. The solvent was distilled under reduced pressure and the residue dissolved in 350 mL of water. The slurry of white crystals and the almost clear solution was extracted thrice with 80 mL of chloroform. The aqueous layer was acidified to pH 4 with concentrated HCl and the white precipitate that formed was allowed to stand overnight prior to filtration. The crystals were dried at 50° C. under high vacuum for 5 hours to yield 106.5 g (0.4416 mol) (92%) of methyl 6-n-Pentyl-2-hydroxy-4-oxo-cyclohex-2-ene-1-carboxylate (mp 96-98 C). The product was recrystallized using a mixture of petroleum ether:ethyl acetate (9:1), and gave 94 g of pure methyl 6-n-Pentyl-2-hydroxy-4-oxo-cyclohex-2-ene-1-carboxylate (melting point of 98-100 C).

B. 1-n-Pentyl-3,5-dihydroxybenzene (Olivetol)

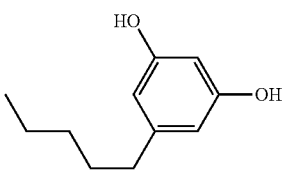

To a stirring ice-cooled solution of methyl 6-N-pentyl-2-hydroxy-4-oxo-cyclohex-2-ene-1-carboxylate (58.4 g, 0.24 mol) dissolved in 115 mL dimethylformamide was added dropwise 37.9 g (0.23 mol) of bromine dissolved in 60 mL of dimethylformamide. At the end of the addition (ca. 90 min) the reaction mixture was slowly heated to 80° C. during which time the evolution of carbon dioxide became quite vigorous.

The reaction was maintained at this temperature until gas evolution had ceased following which the reaction was further heated to 160° C. and held at this temperature for approximately 10 hours. After heating, the reaction was allowed to cool and the solvent DMF was removed under reduced pressure. The residue thus obtained was treated with water (80 mL) and extracted twice with 250 mL of ether. The combined ether layers were washed with water, then washed with 2×80 mL of a 10% solution of sodium bisulfite, 2×80 mL of a 10% solution of acetic acid, and then again with water.

After drying over anhydrous sodium sulfate the solvent was removed under reduced pressure to give 46.8 g of viscous oil. The oil was distilled under reduced pressure to give 30.3 g (0.168 mol) (69.3%) of olivetol as product. HPLC analysis indicated 97.5% purity.

Example 2: Synthesis of 2-[(2E)-3,7-dimethylocta-2,6-dienyl]-5-pentyl-benzene-1,3-diol (Cannabigerol (CBG)

CBG was synthesized following the protocol disclosed by Taura et al., (1996), *The Journal of Biological Chemistry*, Vol. 271, No. 21, p. 17411-17416.

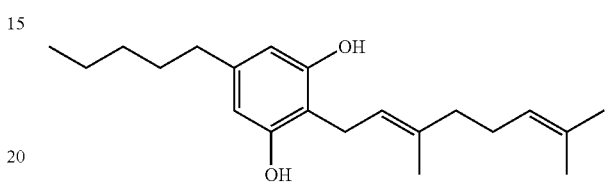

Geraniol (3 g, 0.0194 mol) and olivetol (2 g, 0.0111 mol) were dissolved in 400 mL of chloroform containing 80 mg of p-toluenesulfonic acid as catalyst and the reaction mixture was stirred at room temperature for 12 h in the dark. After 12 hours, the reaction mixture was washed with saturated sodium bicarbonate (400 mL) and then with $H_2O$ (400 mL). The chloroform layer was concentrated at 40° C. under reduced pressure, and the residue obtained was chromatographed on a 2.0 cm×25 cm silica gel column using benzene (1000 mL) as the eluent to give 1.4 g (0.00442 mol) (39.9%) CBG as product.

Alternatively crude CBG was purified as follows. To a 250 mL beaker was added 7.25 g crude CBG and 50 mL benzene. The flask was swirled to dissolve the CBG and 50 g silica gel was added, along with a stir bar. The solution was stirred overnight, and then poured into a 44 cm×2.75 cm column. The column was eluted with 300 mL benzene. The eluent, approximately 70 mL fractions were assayed for CBG. Fractions 1, 2, and 3 (~230 mL) that contained CBG were combined and the solvent removed under pressure to give 6.464 g residue containing >80% CBG, having a purity suitable for use in the next synthetic step.

In one embodiment, crude CBG was purified by mixing 7.25 g crude CBG residue with a slurry of silica gel (50 mL), in a 250 ml Beaker. This mixture was slowly agitated for 1 hour and then vacuum filtered using a fine mesh filter paper. The filter cake was washed with 250 ml benzene until a clear filtrate was obtained. The solvent from the filtrate was removed under reduced pressure to give 6.567 g of a residue having >80% CBG.

Example 3: Synthesis of Methylmagnesium Carbonate (MMC)

Methylmagnesium carbonate (MMC) was synthesized following the protocol disclosed by Balasubrahmanyam et al., (1973), *Organic Synthesis, Collective Volume V*, John Wiley & Sons, Inc., p. 439-444.

A dry 2 L, three necked flask was fitted with a mechanical stirrer, a condenser, and a IL, pressure-equalizing addition funnel, the top of which was fitted with a gas inlet tube. A clean, dry magnesium ribbon (40.0 g, 1.65 mol) was placed in the flask and the system was flushed with nitrogen prior to the addition of anhydrous methanol (600 mL). The evolution of hydrogen gas was controlled by cooling the reaction mixture. When hydrogen evolution had ceased, a slow stream of nitrogen was passed through the system and the condenser was replaced by a total condensation-partial take-off distillation head. The nitrogen flow was stopped and the bulk of the methanol distilled from the solution under reduced pressure. Distillation was stopped when stirring of the pasty suspension of magnesium methoxide was no longer practical. The system was again flushed using nitrogen and the outlet from the distillation head was attached to a small trap containing mineral oil so that the volume of gas escaping from the reaction system could be estimated.

Anhydrous dimethylformamide (DMF)(700 mL) was added to the reaction flask, and the resulting suspension was stirred vigorously while a stream of anhydrous carbon dioxide was passed into the reaction vessel through the gas inlet tube attached to the addition funnel. The dissolution of carbon dioxide was accompanied by an exothermic reaction with the suspended magnesium methoxide. When no more $CO_2$ is absorbed, the colorless solution was heated under a slow stream of $CO_2$ gas until the temperature of the liquid distilling reached 140° C., indicating that residual methanol had been removed from the reaction mixture. The reaction mixture was flushed using a slow stream of nitrogen to aid in cooling the mixture to room temperature under an inert atmosphere. This yielded a solution having 536 mg MMC/mL of DMF.

Example 4: Synthesis of CBGA 6-carboxylic acid-2-[(2E)-3,7-dimethylocta-2,6-dienyl]-5-pentyl-benzene-1,3-diol, Cannabigerolic Acid (CBGA) was prepared as follows. To a 10 mL conical flask was added 1 mL of a DMF solution of MMC. To this solution was added 2-[(2E)-3,7-dimethylocta-2,6-dienyl]-5-pentyl-benzene-1,3-diol (120 mg, 0.379 mmol). The flask was heated at 120° C. for 1 hour, following which the reaction mixture was dissolved in 100 mL of chloroform:methanol (2:1) solution. The pH of this solution was adjusted with dilute HCl to pH 2.0, and then partitioned using 50 mL $H_2O$.

The organic layer was dried over sodium sulfate and the solvent was removed by evaporation. HPLC analysis of the crude reaction showed ~40% conversion of CBG to CBGA.

Alternatively, 3.16 g (10 mmols) of CBG (or any other neutral cannabinoid), 8.63 g (100 mmols) magnesium methylate and 44 g (1 mol) of dry ice were sealed in a pressure compatible vessel. The vessel is heated to 50° C., and the temperature held at this value for three hours. Following heating, the vessel is cooled to room temperature and slowly vented. The reaction mixture was dissolved in 100 mL of a chloroform:methanol (2:1) solvent. The pH of this solution was adjusted with dilute HCl to pH 2.0 and this solution was then partitioned using 50 mL of $H_2O$. The organic layer was dried over sodium sulfate and the solvent was removed by evaporation. HPLC analysis of crude reaction mixture showed ~85% conversion of CBG to CBGA using this protocol.

Crude CBGA was purified by chromatography using a 2.0 cm×25 cm silica gel column. The product was eluted using a mixture of n-hexane:ethyl acetate (2:1) (1000 mL), to obtain 45 mg (0.125 mmol) (37.5%) of the desired product.

Alternatively, ultra high purity CBGA was obtained by chromatographing the crude using LH-20 lipophilic resin as the medium. 400 g of LH-20 Sephadex resin was first swollen using 2 L of DCM:chloroform (4:1) solvent. The swollen resin was gravity packed in a 44×2.75 cm column. The column was loaded with 2.1 g of crude CBGA dissolved in a minimum amount of DCM:chloroform (4:1) solvent and eluted with 1.7 L of the same solvent. 100 mL fractions were collected. The unreacted CBG was eluted as a yellow/orange solution using this solvent system. After the passage of about 1.7 L of this solvent, no more yellow/orange fraction were observed and the eluting solvent was changed to 100%, acetone to elute the bound CBGA.

The fractions containing CBGA were pooled and the solvent was removed to obtain 0.52 g CBGA (~90% recovery). Increasing the volume of DCM:chloroform (4:1) solvent passed through the column prior to eluting with acetone, yielded CBGA having purity greater than 99.5%.

Example 5: Synthesis of CBGV

A. Methyl 6-N-Propyl-2-hydroxy-4-oxo-cyclohex-2-ene-1-carboxylate

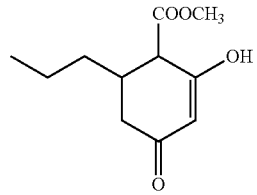

3-hepten-2-one (30.1 g, 0.25 mol) was added dropwise to a dry methanolic (125 mL dry MeOH), solution of diethyl malonate (52.016 g, 0.323 mol) and sodium methoxide (16.206 g, 0.3 mol). The crude product weighed 46.315 g upon drying at 45° C. overnight in a vacuum oven. The crude product was dissolved in petroleum ether (300 mL). After stirring, any undissolved material was filtered from the solution prior to the addition of ethyl acetate (30 mL), to precipitate CBGV. The precipitate was filtered and dried overnight at 44° C. in a vacuum oven. A total of 33.569 g (0.157 mol) (52.3%) of the desired product was recovered.

B. 1-N-Propyl-3,5-dihydroxybenzene

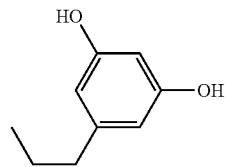

A procedure similar to the one described above for the synthesis of olivetol was used to manufacture the titled compound, except that methyl 6-N-propyl-2-hydroxy-4-oxo-cyclohex-2-ene-1-carboxylate was used as the starting material. Briefly, to a stirring ice cold DMF solution of methyl 6-N-propyl-2-hydroxy-4-oxo-cyclohex-2-ene-1-carboxylate was added a DMF solution of bromine. Following the addition of bromine the reaction mixture was heated to 80° C., which cause the release of carbon dioxide gas. After gas evolution has ceased, the temperature of the reaction was increased to 160° C. and heating was continued for 10 hours. The reaction was then cooled and DMF was removed under reduced pressure. The crude mixture was diluted with water and subjected to solvent extraction using diethyl ether. 1-N-Propyl-3,5-dihydroxybenzene was obtained by removing ether under vacuum, and distilling the remaining oil.

C. 2-[(2E)-3,7-dimethylocta-2,6-dienyl]-5-propyl-benzene-1,3-diol, (CBGV)

The synthesis of CBGV proceeded by adding p-toluenesulfonic acid to a chloroform solution of geraniol and 1-N-Propyl-3,5-dihydroxybenzene. After stirring the reaction at room temperature in the dark for 12 hours, water was added to partition the crude product into the chloroform layer. The chloroform layer was then washed with saturated sodium bicarbonate, dried and the organic solvent removed prior to purification as described above for the synthesis of CBG.

D. 6-carboxylic acid-2-[(2E)-3,7-dimethylocta-2,6-dienyl]-5-propyl-benzene-1,3-diol (CBGVA)

6-carboxylic acid-2-[(2E)-3,7-dimethylocta-2,6-dienyl]-5-propyl-benzene-1,3-diol, cannabigerolic Acid (CBGVA) was prepared as follows. Methyl magnesium carbonate (MMC) was prepared as described above. To a DMF solution of MMC in a flask was added 2-[(2E)-3,7-dimethylocta-2,6-dienyl]-5-propyl-benzene-1,3-diol. The flask was heated at 120° C. for 1 hour, following which the reaction mixture was dissolved in a 2:1 mixture of chloroform:methanol. The pH of this solution was adjusted with dilute HCl to pH 2.0, and the reaction mixture was extracted using $H_2O$.

The organic layer was dried over sodium sulfate and the solvent was removed by evaporation to afford the titled compound CBGVA as the crude product.

Example 6: Synthesis of 2,4-dihydroxy-6-propyl Benzoic Acid Methyl Ester

A. Synthesis of 4-(piperazine-1-carbonyl)-1,3-dihydroxybenzene

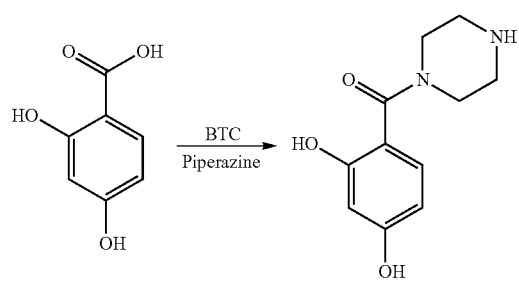

To a cold stirring solution of 2,4-dihydroxybenzoic acid (3.0 eq.) in tetrahydrofuran (or dichloromethane) is added bis(trichloromethyl)carbonate (BTC, 1.0 eq.) and 2,4,6-collidine (base, 3-5 eq.). After stirring at room temperature for about 15 minutes, piperazine (1.5 eq.) is added and the reaction mixture is stirred at room temperature, while reaction progress is periodically monitored by TLC. After the reaction is complete, the reaction mixture is quenched by dilution with water and then extracted with dichloromethane. The organic layer containing crude 4-(piperazine-1-carbonyl)-1,3-dihydroxybenzene is dried over magnesium sulfate and then concentrated to obtain crude 4-(piperazine-1-carbonyl)-1,3-dihydroxybenzene which is purified by silica gel column chromatography.

B. Synthesis of 5-propyl-4-(piperazine-1-carbonyl)-1,3-diol

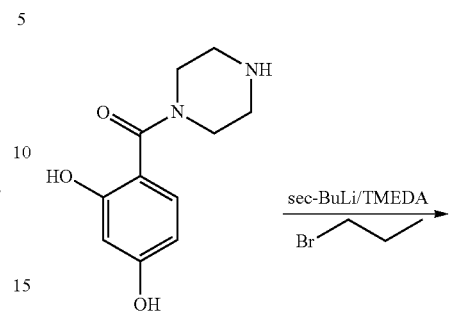

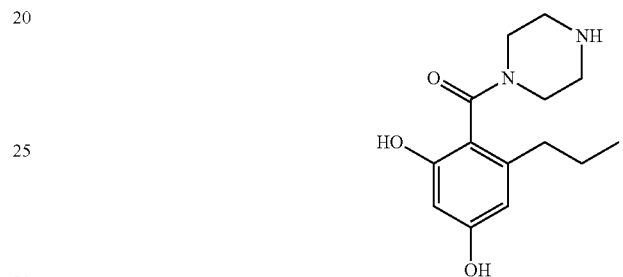

To a solution of 4-(piperazine-1-carbonyl)-1,3-dihydroxybenzene (1.0 eq.) in THF at −78° C. is added dropwise a solution of sec-BuLi (1.2 eq.). The reaction mixture is stirred at −78° C. for approximately 1 h before the dropwise addition of 1-bromopropane. After further stirring of the reaction mixture at −78° C. for 1 h, the reaction flask is gradually permitted to warm to room temperature and stirring continued until TLC indicates complete formation of the desired product 5-propyl-4-(piperazine-1-carbonyl)-1,3-diol. After the reaction is complete, the reaction mixture is cooled to 0° C. prior to quenching using saturated ammonium chloride followed by the addition of HCl. The quenched aqueous solution is extracted using ethyl acetate or diethyl ether. The combined organic layers are dried using magnesium sulfate and the solvent removed under pressure prior to purification of the crude product by silica gel column chromatography.

C. Synthesis of methyl-2,4-dihydroxy-6-propyl Benzoate

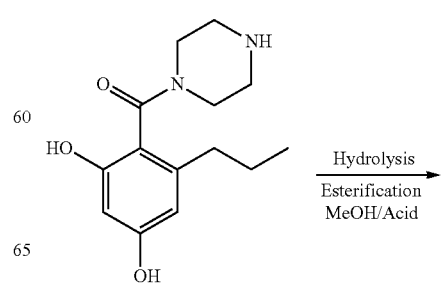

-continued

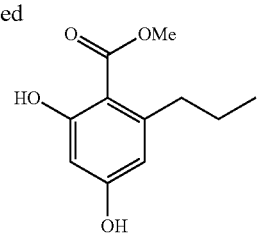

Hydrolysis: A slurry of potassium tert-butoxide in water is added to a THF (or diethyl ether) solution of 5-propyl-4-(piperazine-1-carbonyl)-1,3-diol. The reaction mixture is stirred vigorously at room temperature and progress of the hydrolysis reaction monitored by TLC. (Note: The reaction mixture may be refluxed if necessary to aid hydrolysis). After hydrolysis is complete, the reaction mixture is cooled and neutralized by the dropwise addition of HCl. Following neutralization, 2,4-dihydroxy-6-propyl benzoic acid is extracted into ethylacetate (or diethyl ether) and the organic solvent is removed under reduced pressure.

Esterification: 2,4-dihydroxy-6-propyl benzoic acid is dissolved in methanol followed by the addition of a catalytic amount (few drops) of concentrated sulfuric acid. The resultant methanolic solution is refluxed. When the reaction is complete, the solvent is removed and the crude product is dissolved in ethyl acetate. The ethyl acetate solution is washed with water and then brine. The combined organic layer is dried over magnesium sulfate, concentrated and purified using silica gel column chromatography.

Example 7: Alternative Synthesis of 2,4-dihydroxy-6-propyl Benzoic Acid Ethyl Ester

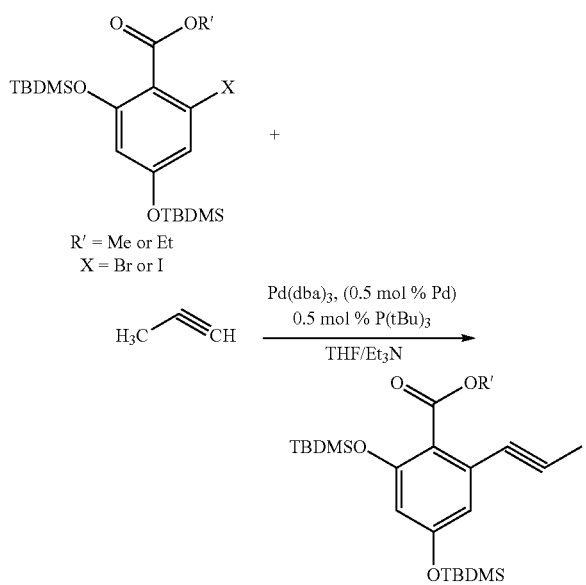

An anhydrous THF solution of an aryl halide shown above (1.0 eq.) maintained under an inert atmosphere of nitrogen is added dropwise to a stirring solution of $Pd_2(dba)_3$ (0.5 mol %) and $P(tBu)_3$ (0.5 mol %) and triethylamine. A solution of propyne is then added and the reaction mixture is stirred at room temperature overnight. After the reaction is complete, the reaction mixture is filtered, concentrated, and purified using silica gel column chromatography. Fractions containing the desired product are pooled together and the solvent evaporated to give ethyl 2,4-bis((t-butyldimethylsilyl)oxy-6-prop-1-yn-1-yl)benzoate as a solid.

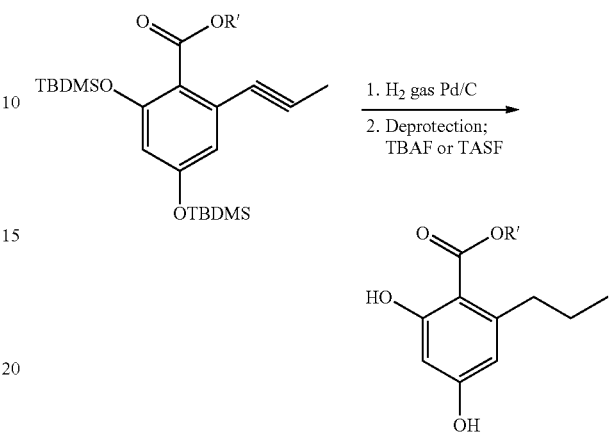

To a degassed THF solution of ethyl 2,4-bis((t-butyldimethylsilyl)oxy-6-prop-1-yn-1-yl)benzoate maintained under an atmosphere of nitrogen is added a catalytic amount of Pd/C (0.1 mol %). Hydrogen gas is then bubbled into the stirring solution while monitoring progress of hydrogenation by TLC. After hydrogenation is complete, the reaction mixture is filtered to remove catalyst and the solvent is evaporated to leave ethyl 2,4-bis(t-butyldimethylsilyl)oxy-6-propylbenzoate. Removal of the t-butyldimethylsilyl protecting groups from ethyl 2,4-bis(t-butyldimethylsilyl)oxy-6-propylbenzoate gives ethyl 2,4-dihyroxy-6-propylbenzoate.

While Examples 6 and 7 illustrate synthetic methodologies wherein $R^1$ is methyl or ethyl, corresponding to methyl and ethyl esters, respectively, the skilled person will recognize that other esters are suitable for use in the methodologies. Examples include other alkyl esters, as "alkyl" is defined hereinabove.

Example 8A: Synthesis of a Formula I Compound, Methyl-3-(3,7-dimethylocta-2,6-dien-1-yl)2,4-dihyroxy-6-propylbenzoate

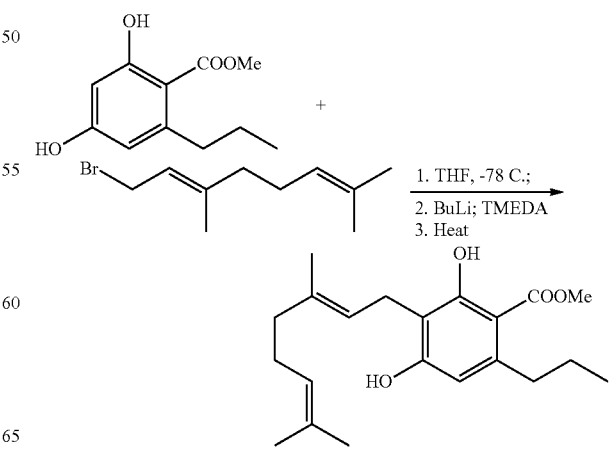

To a THF solution of methyl-2,4-bis((t-butyldimethylsilyl)oxy)-6-propylbenzoate (1.0 eq) at −78° C. was added a solution of butyl lithium (2.0 eq), followed by the addition of TMEDA (1.0-2.0 eq). After stirring for about 15 minutes, geranylbromide (1.5-2.0 eq) was added and the reaction mixture was allowed to warm to room temperature, followed by heating to about 60° C. to 70° C. Reaction progress was monitored by TLC or HPLC-MS chromatography. After the reaction was complete, the crude mixture was permitted to cool to room temperature and then diluted with 5% citric acid. The aqueous solution was extracted three times with ethyl acetate or diethyl ether and the combined organic layers were dried using magnesium sulfate. The crude product was obtained by evaporation of the organic solvent. Purification was effected by silica gel chromatography. The fractions corresponding to the desired product were pooled and concentrated in vacuo to provide methyl-3-(3,7-dimethylocta-2,6-dien-1-yl)2,4-dihyroxy-6-propylbenzoate. If necessary a second purification was effected by titurating the product obtained from the silica gel column with hexane or heptane.

Alternatively, purification was accomplished by dissolving the crude product in a minimum volume of ethyl acetate or diethyl ether and then precipitating methyl-3-(3,7-dimethylocta-2,6-dien-1-yl)2,4-dihyroxy-6-propylbenzoate by the addition of hexane or heptanes.

Example 8B: Alternative Synthesis of a Formula I Compound, Methyl-3-(3,7-dimethylocta-2,6-dien-1-yl)2,4-dihyroxy-6-propylbenzoate

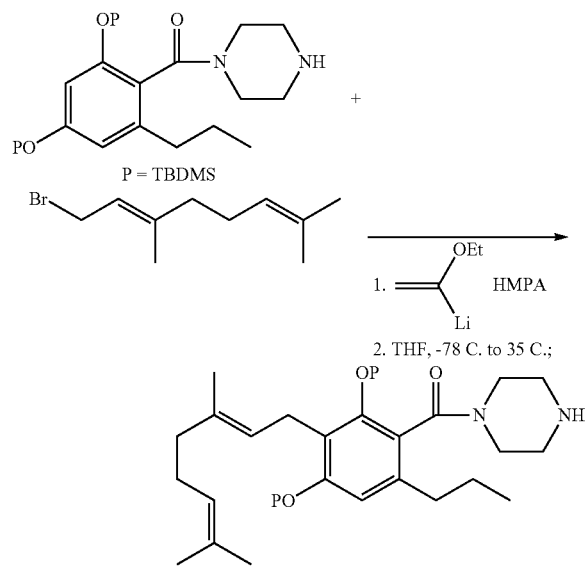

HMPA and ethoxy vinyl lithium are added to a THF solution of 2,4-bis((t-butyldimethylsilyl)oxy)-6-propylphenyl piperazin-1-methanone at −78° C. After stirring for about 15 minutes, geranylbromide (1.5-2.0 eq), is added and the reaction mixture stirred at −78° C. for 5-60 minutes before permitting it to warm to room temperature. The reaction mixture is then heated to about 35° C. to 65° C. and progress is monitored by TLC or HPLC-MS chromatography. After the reaction is complete, the crude mixture is permitted to cool to room temperature and then diluted with 5% citric acid. The aqueous solution is extracted with three volumes of ethyl acetate or diethyl ether and the combined organic layers are dried using magnesium sulfate. The crude product is obtained by evaporation of the organic solvent. Purification is carried out by silica gel chromatography. The fractions corresponding to the desired product are pooled and concentrated in vacuo to provide methyl-3-(3,7-dimethylocta-2,6-dien-1-yl)2,4-dihyroxy-6-propylbenzoate. If necessary a second purification is effected by titurating the product obtained from the silica gel column with hexane or heptane.

Example 9: Enzyme Catalyzed Synthesis of THC-v, CBV, and CBN

The standard assay conditions to monitor the enzyme-catalyzed formation of THC-v, CBV and CBN are as follows. Small-scale synthesis of cannabinoids entails use of 1.5 ml Eppendorf snap cap tubes. 25 µl of a substrate such as CBGA or CBGVA, is dissolved in DMSO at a concentration of 1.0 mg/ml. An aliquot of the substrate is added to 25 µl of an enzyme solution dissolved in 200 µl of 100 mM citrate buffer, pH 4.85, and the resultant solution is incubated at 30° C. for 2 hours. Enzymatic catalyzed synthesis is terminated by adding 250 µl of MeOH and formation of product is analyzed by HPLC.

To optimize the synthesis of cannabinoids, the effect of solvent composition, reaction time, and pH on enzyme activity are tested as follows:
1. Different solvents or mixtures of solvents as described above are tested to enhance substrate solubility and improve reaction kinetics;
2. Catalysis is performed for each substrate at different pH values, for example, at a pH of 4, 5, 6, 7, and 8;
3. Enzyme assays is run in either sodium phosphate buffer or citrate buffer with or without SDS or Triton-X. Some assays are run in a mixed solvent system and will include DMSO, DMF, IPA, or cyclodextrin (CD) at varying concentrations; and
4. Bioenzymatic synthesis of THC-v, CBV or CBN are monitored as a function of time, for example, by analysis of the reaction mixture over a time interval of about 1 minute to about 4 days.

For illustrative purposes, the synthesis of THC-v and CBV using the claimed method proceeds as follows. Catalysis is performed in a solvent that contains cyclodextrin, for example, 2-hydroxypropyl-β-cyclodextrin (HPβCD; Kleptose® HPB), sulfobutylether β-cyclodextrin sodium salt (SBEβCD; Captisol®), or a randomly methylated β-cyclodextrin (RMIβCD; concentration 35 g/L), by adding a known amount of the cyclodextrin to a 10 mM sodium phosphate buffer (pH 5.0). The solution is stirred to form a homogenous solution prior to the addition of a Formula I compound such as CBGVA (R is —COOH and $R^1$ is propyl). After mixing the solution at room temperature for 1-2 min, a buffered solution of the appropriate cannabinoid synthase, for example THCVA synthase or THCA synthase is added and the reaction mixture is incubated at 30° C. for a fixed amount of time. At uniform intervals of time, aliquots (10 µl) of the reaction mixture are taken and added to an Eppendorf tube containing ethanol (50 µl), to denature the enzyme. After centrifugation at 10,000 rpm for 5 minutes, the ethanol layer is separated from the denatured protein precipitate, transferred to a clean Eppendorf tube and the solvent evaporated using a stream of nitrogen.

The residue thus obtained is reconstituted in buffer and the progress of the enzyme catalyzed formation of a Formula II compound is quantitated by reverse-phase HPLC.

Alternatively, the reaction mixture is diluted 10:1 with 95% EtOH to cause cyclodextrin to precipitate out while leaving the cannabinoids as well as unreacted Formula I compound in solution. After removing the supernatant the solvent is evaporated and the residue thus obtained is analyzed by HPLC after reconstitution in buffer.

The precipitate of cyclodextrin is washed with an excess of 90% EtOH, and dried to permit its reuse in a future reaction.

The Formula II compound obtained using the method described above is THCVA. The desired cannabinoid THC-v is obtained by decarboxylation of THCVA using one the protocols described above.

The synthesis of CBV is accomplished by oxidizing THC-v. Briefly, oxidation is accomplished by exposing rapidly stirred, dilute solution of THC-v to UV-light for 1-24 hours or by bubbling a stream of air into a rapidly stirred solution of THC-v. Progress of the oxidation is monitored by HPLC or UV-spectroscopy and the oxidation reaction is halted once oxidation is complete.

A similar method is used to produce the cannabinoid CBN. For instance, synthesis of CBN using the inventive method proceeds by contacting CBGA with the enzyme THCA synthase to produce the Formula II compound tetrahydrocannabinolic acid (THCA). Oxidation of THCA using a method described above provides CBNA, which is decarboxylated by contacting a solution of CBNA with heat to obtain CBN.

C. Purification of CBN, CBV, and THC-v

The cannabinoids synthesized using the inventive bioenzymatic reactions described above are purified by HPLC and fractions corresponding to the desired product are pooled and lyophilized to dryness prior to their use as pharmaceutical agents.

D. Therapeutic Applications of THC-v, CBV and CBN

Of all the naturally occurring cannabinoids, tetrahydrocannabinol (THC) is gaining acceptance as a therapeutic for treating a wide range of medical conditions, including glaucoma, obesity, AIDS wasting, neuropathic pain, treatment of spasticity associated with multiple sclerosis, fibromyalgia and chemotherapy-induced nausea. THC is also effective in the treatment of allergies, inflammation, infection, epilepsy, depression, migraine, bipolar disorders, anxiety disorder, drug dependency and drug withdrawal syndromes. However, THC is habit forming and is known to cause temporary impairment of neurological functions. Accordingly, significant efforts are being made to identify other phytocannabinoids or analogs of cannabinoids that retain the medicinal properties without the psychotic or dependence activity exhibited by THC.

In this regard, several studies have indicated that the three carbon homologue THC-v, as well as the oxidized forms of THC-v and THC retain many of the therapeutic properties of THC without the psychotic activity of this cannabinoid.

The present invention provides a method for the large-scale synthesis of THC-v, CBN and CBV as well as pharmaceutically acceptable formulations of these cannabinoids as therapeutics for treating the above mentioned disorders. For instance, the effect of THC-v to reduce or ameliorate insulin sensitivity which is implicated to play a role in diabetes and obesity is well known. See, Wargent, E. T. et al., Nutr. Diabetes, Vol. 3(5), 2013. Thus, the present invention provides THC-v as a therapeutic agent for reducing body fat in ob/ob mice.

The neuroprotective role of THC-v as well as its effect in relieving the symptoms of Parkinson's Disease is also well known. See Garcia, C. et al., Br. J. Pharmacol., 2011, 163(7): p 1495-1506. The present invention provides THC-v as a therapeutic agent to reduce motor inhibition and provide neuroprotection to rats whose brains were lesioned by the administration of 6-hydrodopamine or lipopolysaccharides. See Vasant, S., Mol. Neurodegener., 2015; 10: 17.

We claim:

1. A method for producing a compound of Formula III:

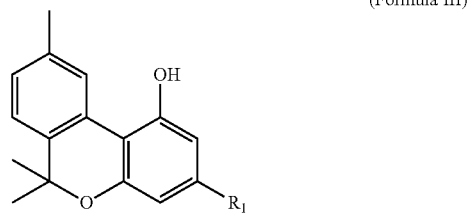

(Formula III)

wherein $R_1$ is n-propyl or n-pentyl, comprising the steps of contacting a compound of Formula I

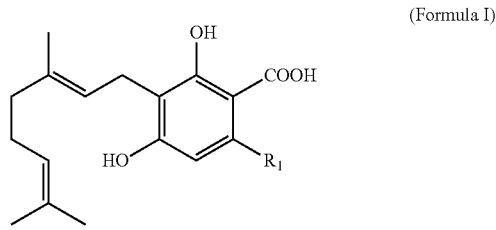

(Formula I)

in a mixture comprising an aqueous buffer and at least one organic solvent selected from the group consisting of methanol, ethanol, propanol, isopropanol, acetone, dimethylsulfoxide, hexane, and ethylacetate with a cannabinoid synthase to produce a compound of Formula II:

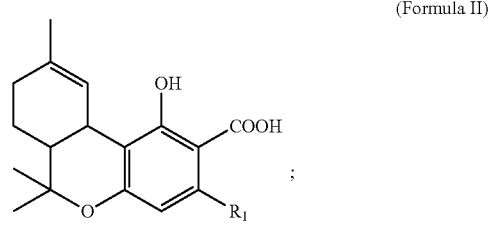

(Formula II)

;

and either (A1) oxidizing the compound of Formula II to produce a compound of Formula A:

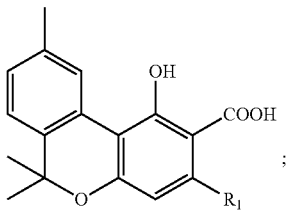

and (A2) de-carboxylating the compound and of Formula A to produce the compound of Formula III;

OR (B1) de-carboxylating the compound of Formula II to produce a compound of Formula B:

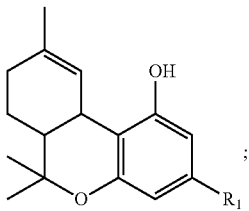

and (B2) oxidizing the compound of Formula B to produce the compound of Formula III.

2. The method of claim 1, wherein the cannabinoid synthase is a tetrahydrocannabinolic acid (THCA) synthase.

3. The method of claim 2, wherein $R_1$ is n-pentyl.

4. The method of claim 2, wherein $R_1$ is n-propyl.

5. The method of 1, wherein the compound of Formula II is subjected to steps (A1) and (A2).

6. The method of claim 1, wherein the compound of Formula II is subjected to steps (B1) and (B2).

7. The method of claim 1, wherein the de-carboxylating step comprises exposing the compound of Formula A or Formula II to heat, UV light, or a weak base.

8. The method of claim 1, wherein the oxidizing step comprises exposing the compound of Formula II or Formula B to air, oxygen, gas, an oxidizing agent, an oxidation catalyst, UV-light, or a combination thereof.

9. The method of claim 1, wherein the organic solvent is dimethylsulfoxide.

10. The method of claim 1, wherein the aqueous buffer is selected from the group consisting of citrate buffer, phosphate buffer, HEPES buffer, Tris buffer, MOPS buffer, or glycine buffer.

11. The method of claim 1, wherein $R_1$ is n-pentyl, the cannabinoid synthase is a tetrahydrocannabinolic acid (THCA) synthase; and the compound of Formula II is subjected to steps (B1) and (B2).

12. The method of claim 1, wherein $R_1$ is n-pentyl, the cannabinoid synthase is a tetrahydrocannabinolic acid (THCA) synthase; and the compound of Formula II is subjected to steps (A1) and (A2).

13. The method of claim 1, wherein $R_1$ is n-propyl, the cannabinoid synthase is a tetrahydrocannabinolic acid (THCA) synthase; and the compound of Formula II is subjected to steps (B1) and (B2).

14. The method of claim 1, wherein $R_1$ is n-propyl, the cannabinoid synthase is a tetrahydrocannabinolic acid (THCA) synthase; and the compound of Formula II is subjected to steps (A1) and (A2).

15. The method of claim 1, wherein the concentration of the organic solvent is between 10% and 90% (v/v).

16. The method of claim 1, wherein the concentration of the organic solvent is between 10% and 30% (v/v).

* * * * *